United States Patent [19]

Fazio et al.

[11] Patent Number: 5,039,813
[45] Date of Patent: Aug. 13, 1991

[54] 2-(4-ALKENYLPHENYL)-5-OXAZOLONES AND POLYMERS THEREOF

[75] Inventors: Robert C. Fazio, Yorba Linda, Calif.; Lloyd D. Taylor, Lexington, Mass.

[73] Assignee: Polaroid Corporation, Cambridge, Mass.

[21] Appl. No.: 546,250

[22] Filed: Jun. 29, 1990

[51] Int. Cl.$^5$ ................ C07D 263/08; C07D 263/52; C08F 226/06
[52] U.S. Cl. .................................. 548/228; 526/258; 548/216
[58] Field of Search ................ 526/258; 548/228, 216

[56] References Cited

U.S. PATENT DOCUMENTS

| | | | |
|---|---|---|---|
| 3,583,950 | 6/1971 | Kollinsky et al. | 260/78 |
| 4,070,348 | 1/1978 | Kräemer et al. | 260/79.3 |
| 4,737,560 | 4/1988 | Heilmann et al. | 526/304 |

OTHER PUBLICATIONS

Y. Iwakura et al., Journal of Polymer Science: Part A-1, vol. 6, pp. 2681-2686 (1968).

J. deJersey et al., Biochemistry, vol. 8, No. 5, pp. 1967-1974, May 1969.

L. D. Taylor, et al., Polymer Letters, "Synthesis and Polymerization of 2-Vinyl-4,4-Dimethyl-5-Oxazolone", vol. 9, pp. 187-190 (1971).

L. D. Taylor, et al., Makaromol. Chem. Rapid Commun., "Synthesis of Poly(4,4-dimethyl-2-vinyl-5-oxazolone) an Interesting Material for Preparing Polymeric Agents", vol. 3, pp. 779-782 (1982).

J. K. Rasmussen, et al., Advances in Polymer Synthesis, B. M. Culbertson and J. E. McGrath, Editors, Plenum Publishing Corp., New York, pp. 203-233 (1985).

J. K. Rasmussen, et al., "Polyazlactones", Encycl. Polym. Sci. Eng., Second Edition, H. F. Mark, N. Bikales, C. G. Overberger and G. Menges, Editors, Wiley, New York, NY, vol. 11, pp. 558-571 (1988).

*Primary Examiner*—Joseph L. Schofer
*Assistant Examiner*—Wu C. Cheng
*Attorney, Agent, or Firm*—Louis G. Xiarhos

[57] ABSTRACT

Disclosed are certain 2-(4-alkenylphenyl-5-oxazolones useful in the production of polymers containing pendant functional groups obtained by nucleophilic ring-opening addition reactions, the 2-(4-alkenylphenyl)-5-oxazolones having the formula

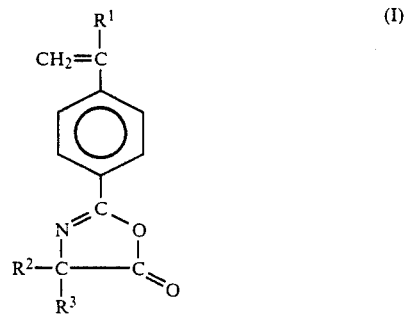

wherein $R^1$ is hydrogen or alkyl; each of $R^2$ and $R^3$ is hydrogen, alkyl, aryl, alkaryl, aralkyl, cycloalkyl, or $R^2$ and $R^3$ together with the carbon atom to which they are bonded constitute a carbocyclic or heterocyclic ring.

5 Claims, No Drawings

2-(4-ALKENYLPHENYL)-5-OXAZOLONES AND POLYMERS THEREOF

BACKGROUND OF THE INVENTION

This invention relates to certain azlactone (oxazolone) compounds. More particularly, it relates to certain 2-alkenylphenyl-5-oxazolones useful in the production of homopolymers and copolymers having pendant functional groups obtained by ring-opening addition to azlactone (oxazolone) groups.

Monomeric and polymeric azlactones (also known as oxazolones) are well known and have been described in numerous patent and other publications. The functionality of their pendant azlactone groups, particularly the reaction of such groups with nucleophilic materials, and without production of by-product materials, has also been reported. For example, polymerizable azlactones, and their use in the production of homopolymers and copolymers having versatility in the production of useful polymeric products, have been described in U.S. Pat. No. 3,488,327 (issued Jan. 6, 1970 to F. Kollinsky et al.); in U.S. Pat. No. 3,583,950 (issued Jun. 8, 1971 to F. Kollinsky et al.); in U.S. Pat. No. 4,304,705 (issued Dec. 8, 1981 to S. M. Heilmmann et al.); in U.S. Pat. No. 4,737,560 (issued Apr. 12, 1988 to S. M. Heilmann et al.); by Iwakura, et al., in Journal of Polymer Science, Vol. 6, pp. 2681–2684 (1968); by L. D. Taylor, et al., in Makromol. Chem., Rapid Commun. 3, 779–782 (1982); and by J. K. Rassmussen, et al., in Encycl. Polm. Sci. Eng., Second Edition, H. F. Mark, N. Bikales, C. G. Overberger and G. Menges, Editors, Wiley, New York, N.Y., Vol. 11, pp. 558–571 (1988).

Among azlactone compounds which have been the focus of considerable attention, by reason of their potential value in the production of highly versatile functional polymers, is the monomer, 2-vinyl-4,4-dimethyl-5-oxazolone, prepared and reported by K. Hübner et al., in Angew. Makromol. Chem. 11, 109 (1970). Reported advantages of this monomer include ease of preparation, stability and reactivity of the anhydride group thereof by addition, with no by-product formation. L. D. Taylor, et al., Makromol. Chem. Rapid Commun. 3, 779–782 (1982). Azlactone polymers in the form of homopolymers are, in general, insoluble in water and only poorly wetted by water. The homopolymer of 2-vinyl-4,4-dimethyl-5-oxazolone (VDMO) is, for example, soluble in organic solvents such as chloroform, dichloromethane, dimethylformamide or tetrahydrofuran, and, if kept very dry, in ethyl acetate, benzene or acetone—as reported by L. D. Taylor, et al., in Makromol. Chem. Rapid Commun. 3, 779–792 (1982). The homopolymer is insoluble in water and poor wettable.

In the production of useful polymeric products from derivatizable azlactone monomers, it will oftentimes be preferred to first form an azlactone polymer having certain predetermined physical and solubility characteristics, in contemplation of the intended use for the derivatized and functional polymeric product, and to then react the azlactone groups of the resulting azlactone polymer with the derivatizing and functionally useful compound. Particularly where the derivatized polymer is to be used in an aqueous medium, the desired properties of the derivatizable azlactone polymer may be the result of copolymerization of a polymerizable monomeric azlactone with another ethylenically unsaturated polymerizable monomer. In general, production of useful derivatizable polymers, and particularly copolymers, will depend upon the polymerizability, i.e., the polymerization reactivity, of the azlactone monomer. For example, an intended production of an azlactone copolymer from an azlactone monomer and another copolymerizable monomer may lead only to an azlactone homopolymer or to the production of a copolymer containing repeating units in proportions substantially different from the proportions of monomers used in the polymerization. Moreover, copolymerizable monomers having desired hydrophilicity will oftentimes contain nucleophilic moieties, such as hydroxyl or amino groups, which may interfere with desired copolymerization by undesired ring-opening reaction with pendant azlactone groups.

If desired, a polymerizable azlactone monomer can be reacted with a functionally useful derivatizing agent prior to production of a homopolymer or copolymer. It will be appreciated that the polymerizability of the derivatized monomer will be influenced by the nature of the moiety introduced into the monomer by such derivatization. The carbon-carbon double bond of the azlactone monomer may also be the site of a competing and undesired reaction during derivatization of the monomer. While the anhydride group of the azlactone heterocycle shows good ring-opening reactivity without by-product formation, it has been reported that certain sulfur compounds and bulky secondary amines react with alkenyl azlactones at the carbon-carbon double bond (by a 1,4- or Michael-addition reaction), and under certain conditions, at the most polarized electrophilic center, i.e., at the carbonyl group (J. K. Rasmussen, et a;., Advances in Polymer Synthesis, B. M. Culbertson and J. E. McGrath, Editors, Plenum Publishing Corp., New York, 1985, p. 230).

It will be appreciated that an alkenyl azlactone monomer which exhibits good polymerization activity, such that homopolymers and copolymers can be readily produced therefrom, and which has the ring-opening reactivity of pendant azlactone groups in monomeric or polymeric form, will be advantageous. A polymerizable alkenyl azlactone which can be derivatized for use in the production of useful polymers, with little or no attending involvement of the alkenyl group in an undesired Michael addition reaction, will be of particular advantage in the production of functional polymeric derivatives.

SUMMARY OF THE INVENTION

The present invention provides a class of polymerizable alkenyl azlactone monomers which exhibit good polymerizability and which can be polymerized with readily available copolymerizable monomers, such as styrene and monomers readily polymerizable with styrene. The monomers have the versatility of the pendant and reactive azlactone groups, such that a variety of useful moieties can be attached thereto by a ring-opening reaction. The monomers may, if desired, be derivatized before polymerization, and with little or no involvement of the polymerizable alkenyl functionality in a Michael addition reaction. According to one composition aspect of the present invention, there is provided a class of 2-(4-alkenylphenyl)-5-oxazolones having the formula (I):

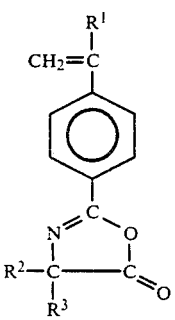

wherein R¹ is hydrogen or alkyl (e.g., methyl); and each of R² and R³ is hydrogen, alkyl (e.g., methyl, ethyl, propyl, isopropyl), aryl (e.g., phenyl, naphthyl), alkaryl (e.g., tolyl), aralkyl (e.g., benzyl), cycloalkyl (e.g., cyclohexyl, adamantyl), or R² and R³ together with the carbon atom to which they are bonded constitute a carbocyclic or heterocyclic ring.

According to another composition aspect of the present invention, there is provided a polymer containing repeating units from a 2-(4-alkenylphenyl)-5-oxazolone and, optionally, repeating units from an ethylenically unsaturated monomer copolymerizable therewith, the polymer having the formula(II)

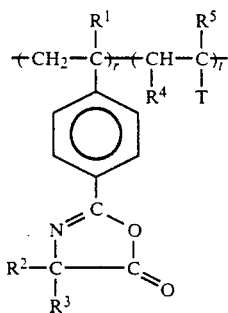

wherein each of R¹, R² and R³ is as previously defined; each of R⁴ and R⁵ is hydrogen or alkyl; T represents the residual pendant atoms of a repeating unit derived from an ethylenically unsaturated monomer copolymerizable with a 2-(4-alkenyl phenyl)-5-oxazolone; and each of r and t represents a mole proportion of each of the respective units, with the proviso that t can be zero. The formula-(II) polymer of the invention, which can be an oxazolone homopolymer or a copolymer of the 2-(4-alkenylphenyl)-5-oxazolone and a copolymerizable monomer, can be used as an intermediate, by reaction of pendant moieties thereof, for the production of a variety of useful polymeric materials.

According to still another compositional aspect of the present invention, there is provided a class of polymers having useful functional groups and having the formula (III)

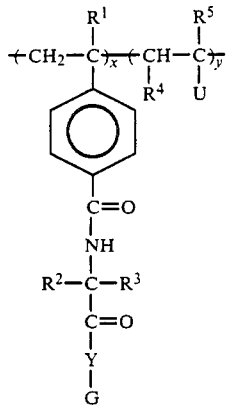

wherein each of R¹, R², R³, R⁴ and R⁵ has the meaning previously defined; Y is —O—, —NH, —NR⁹— or —S—, wherein R⁹ is alkyl or aryl; —Y—G is the residue of a nucleophilic functional agent having an active hydrogen and the formula H—Y—G; U represents the residual pendant atoms of a repeating unit derived from an ethylenically unsaturated monomer copolymerizable with the ethylenically unsaturated monomer which provides said "x" repeating unit or with the corresponding azlactone precursor thereof; and each of subscripts x and y represents a molar proportion of the respective repeating unit represented thereby, with the proviso that y can be zero.

DETAILED DESCRIPTION OF THE INVENTION

As indicated previously, the present invention is directed toward certain 2-(4-alkenylphenyl)-5-oxazolones which can be used as intermediates in the production of polymers having useful pendant groups and which are represented by formula (I). The formula-(I) oxazolones, as can be seen from the following structure

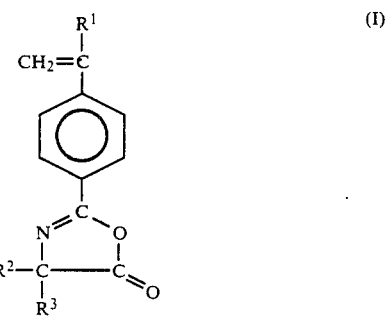

contain an essential alkenyl group (vinyl, in the case where R¹ is hydrogen) which, taken with the phenyl nucleus, constitutes an alkenylphenyl styrene-like group. The alkenylphenyl group is believed to contribute importantly to the capacity of the formula-(I) oxazolones to be readily polymerized with styrene, styrene-like polymerizable monomers and monomers which are polymerizable readily with styrene. Thus, when R¹ is hydrogen, the formula-(I) oxazolone is a 2-(4-vinylphenyl)-5-oxazolone.

The formula-(I) oxazolones of the invention can be prepared by a reaction scheme which, for example, involves (a) the acylation of an α-amino-carboxylic acid, using a 2-alkenyl-benzoyl chloride and (b) a subsequent dehydrative ring closure, which steps are illustrated in Reaction Scheme A, as follows:

Reaction Scheme A:

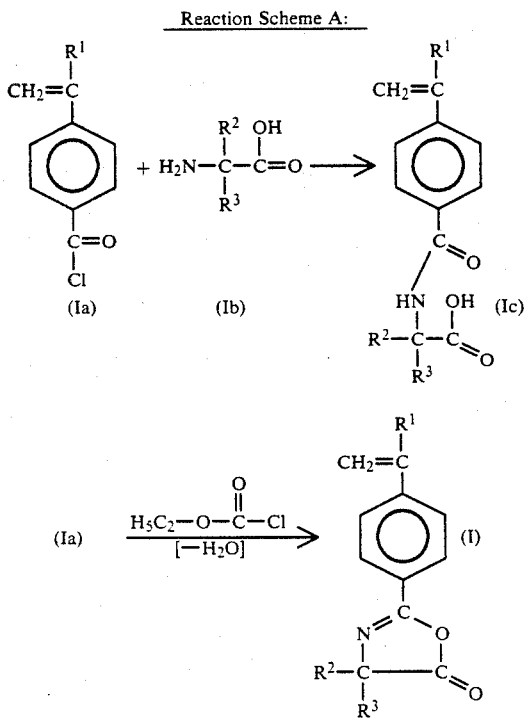

If desired, the formula-(Ia) alkenylbenzoyl chloride can be prepared by reaction of thionyl chloride with the 4-alkenylbenzoic acid (e.g., 4-vinylbenzoic acid), using a procedure such as is described in Macromolecules, Vol. 21, No. 3, 1988 (p.561).

Each of $R^2$ and $R^3$ in the formula-(Ib) intermediate and in the formula-(I) compound of the invention can be hydrogen, if desired. It will be preferred, however, from the standpoints of minimizing undesirable rearrangements and achieving higher yields of purer and more stable compounds, that $R^2$ and $R^3$ substituent groups be other than hydrogen. Inasmuch as hydrogen atoms at the 4-position of the azlactone ring are an active, undesirable Dakin West and/or dimerization reactions can lead to the production of undesired by-products. In this connection, it is noteworthy that isolation of a pure sample of 2-(4-vinylphenyl-5-oxazolone) (derived from paravinylhippuric acid) was not successful. Thus, as in the case or the production of 2-vinyl-5-oxazolones, as reported by L. D. Taylor, et al., in J. Polym. Sci. 8, Vol. 9, 187, (1971), the 4-position of the azlactone ring is desirably substituted with alkyl groups. In general, good results are obtained when the $R^2$ and $R^3$ substituents are alkyl. Especially preferred are the formula-(Ib) intermediates and formula-(I) azlactones wherein each of $R^2$ and $R^3$ is the same alkyl, such as methyl. It will be appreciated that the formula-I(b) reactant, when each of $R^2$ and $R^3$ is the same alkyl, is the aminoacid, 2-methylalanine, which is a preferred reactant for production of the formula-(I) oxazolones of the invention.

The ring-closing step of Reaction Scheme A can be performed using an alkyl haloformate such as ethyl chloroformate, as is described, in connection with the preparation of 2-vinyl-5-oxazolones, by L. D. Taylor, et al., in J. Polym. Sci. B, Vol. 7, 597 (1969). Dehydrative ring-closing reactions, such as are known and described in "Organic Reactions", Vol. 3, 198 (1949), can be adapted to advantage for the conduct of the ring-closing reaction shown in Reaction Scheme A. If desired, benzyl haloformates can be used in the ring-closing reaction. Anhydrides such as acetic anhydride and trifluoroacetic anhydride can be used and the ring-closing methodology of J. W. Lynn, in J. Org. Chem., 24, 1030 (1959) and in Great Britain Patent No. 1,121,418, can be adapted to the reaction scheme shown in Reaction Scheme A.

It will be noted that the $R^1$ group of the formula-(Ia) intermediates and of the formula-(I) oxazolones of the invention can be hydrogen or alkyl. Thus, the ethylenically-unsaturated moiety of the formula-(Ia) and formula-(I) compounds can be vinyl or, for example, isopropenyl. The vinyl azlactones are, however, preferred, from the standpoint of greater reactivity in polymerization reactions.

Examples of 2-(4-alkenylphenyl)-5-oxazolones of formula (I) and useful in the present invention include, for example, 2-(4-vinylphenyl)-5-oxazolone; 2-(4-methyl-4-ethyl-5-oxazolone; 2-(4-vinylphenyl)-4,4-diethyl-5-oxazolone; 2-(4-vinylphenyl)-4,4-diphenyl-5-oxazolone; 2-(4-vinylphenyl)-4-methyl-4-tolyl-5-oxazolone; 2-(4-vinylphenyl)-4,4-dibenzyl-5-oxazolone; 2-(4-vinylphenyl)-4,4-dicyclohexyl-5-oxazolone; and 2-(4-isopropenylphenyl)-4,4-dimethyl-5-oxazolone.

The formula-(I) oxazolones of the invention have certain advantages which adapt them to application in the production of polymers having useful pendant moieties. For example, the compound 2-(4-vinylphenyl)-4,4-dimethyl-5-oxazolone (alternatively, referred to as VPDMO) can be readily synthesized from commercially available materials and can be handled as a white, solid material. This is in contrast to 2-vinyl-4,4-dimethyl-5-oxazolone (VDMO) which is a liquid. VPDMO can be formed into copolymers with vinylbenzyl chloride to provide solid materials which incorporate the desired functionality of vinylbenzyl chloride repeating units.

As noted previously, the formula-(I) oxazolones of the invention have, in part, a structural similarity to styrene. While applicants do not wish to be bound by any precise theory or mechanism in explanation of the ready polymerization of the formula-(I) oxazolones with styrene and other styrene-like monomers, and with compounds commonly polymerized with styrene, the presence of a styrene-like group in the compounds is believed at least in part to be a contributing factor. Styrene can, for example, be polymerized with a formula-(I) oxazolone monomer of the invention using polymerization methods known in the art in relation to styrene polymerizations. Copolymers wherein the repeating units are present in proportions in substantial correspondence with the proportions of starting monomer(s) can be prepared. In addition to styrene, monomers such as acrylonitrile and butadiene, commonly copolymerized with styrene, can be copolymerized with a formula-(I) oxazolone of the invention.

Among copolymers of the invention which contain repeating units derived from a formula-(I) oxazolone are the copolymers represented by formula (II). A variety of copolymerizable monomers can be used to provide the repeating units represented by the mole proportion "t". Preferred ethylenically unsaturated copolymerizable monomers include those of the following formula (IIb)

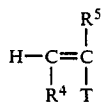

(IIb)

wherein $R^4$ and $R^5$ are hydrogen or alkyl (e.g., methyl) and T represents a group or atoms pendant therefrom. Examples of such monomers include the acrylic and/or methacrylic acid esters, acrylic and/or methacrylic acid, acrylonitrile, methacrylonitrile, acrylamide and/or methacrylamide and/or the N-substitution products of these amides, styrene, vinyl esters, vinyl halides, vinylbenzyl halides, vinyl sulfonic acids, esters of polymerizable dicarboxylic acids such as maleic, fumaric or itaconic acids, and olefins such as isoprene and butadiene and other polymerizable azlactone monomers. It will be appreciated that the pendant moiety

—T of the formula-(II) copolymers will typically be an organic group comprising all of the atoms of the repeating unit derived from the copolymerizable formula-(IIb) monomer, exclusive of the unsaturated carbon atoms and the $R^4$ and $R^5$ moieties. These monomers are well known and examples of monomers useful for the purpose of preparing formula-(II) oxazalone copolymers can be found in U.S. Pat. No. 3,488,327 (issued Jan. 6, 1970 to F. Kollinsky, et al.) and in U.S. Pat. No. 3,583,950 (issued Jun. 8, 1971 to F. Kollinsky et al.). Examples of other polymerizable azlactones include those described in U.S. Pat. Nos. 3,488,327 and 3,583,950 and those used in the production of our azlactone copolymers described and claimed in our copending patent application, Ser. No. 370,809, filed Jun. 23, 1989, now U.S. Pat. No. 4,981,933, issued Jan. 1, 1990.

The molar proportions of the "r" and "t" repeating units of the formula-(II) polymers can vary widely. The polymers will be homopolymers when "t" is zero. Copolymers can be prepared by copolymerization of the formula-(I) and formula-(IIb) monomers using a variety of polymerization methods, such as solution, bulk, suspension and emulsion polymerization methods. The polymerization can be initiated chemically, e.g., by suitable free-radical or redox initiation or by other means, such as heat or incident radiation. As examples of chemical initiators, mention may be made of 2,2'-azobisisobutyronitrile, potassium persulfate, sodium bisulfite, benzoyl peroxide, diacetyl peroxide, hydrogen peroxide and diazoaminobenzene. It will be appreciated that the chosen means of initiation should be substantially incapable of degrading or otherwise adversely reacting with either reactants or products of the reaction. The amount of catalyst used and the reaction temperature may be varied to suit particular needs. Generally, the polymerization should proceed satisfactorily by carrying out the reaction at a temperature between 25° C. and 100° C. and using less than 5% by weight of initiator, based on the starting weight of the polymerizable monomer or monomers.

The proportions of formula-(I) and formula-(IIb) comonomers can vary, for example, in a molar range of from 1:99 to 99:1. In general, the azlactone repeating units will be of primary importance for their versatility as derivatizable units and will be present in the copolymers such that the ratio of "r" and "t" repeating units is in the range of from 1:9 to 9:1, and especially, from 1:4 to 4:1. Particular ratios can vary depending upon the desired derivatizations to be performed and on the applications intended for the derivatized copolymers.

Polymerization techniques that can be modified by inclusion of the copolymerizable formula-(I) monomer are those described, for example by L. D. Taylor, et al., J. Polym. Sci. B, Vol. 9, 187 (1971); by Iwakura, et al., J. Polym. Sci., A-1, Vol. 6, 2681 (1968); in U.S. Pat. No. 3,488,327; in U.S. Pat. No. 3,583,950; and in Great Britain Pat. No. 1,121,418.

Preferred formula-(IIb) monomers for copolymerization include styrene, vinylbenzyl halides (e.g., vinylbenzyl chloride) and mixtures thereof. A preferred class of copolymers contains repeating units according to the formula (IIc)

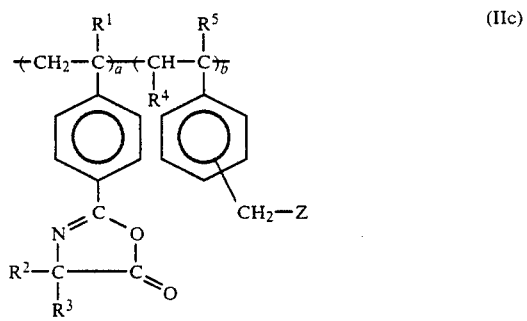

wherein each of $R^1$, $R^2$, $R^3$, $R^4$ and $R^5$ has the meaning previously defined; a and b represent molar proportions in the range of 1:99 to 99:1 (preferably 1:9 to 9:1, especially 1:4 to 4:1); and Z is halogen, such as chlorine. The formula-(IIc) copolymers include repeating units from a copolymerizable alkenylbenzyl halide. Each of $R^4$ and $R^5$ can be hydrogen or alkyl (e.g., alkyl of from 1 to 6 carbon atoms). Preferably, each of $R^4$ and $R^5$ will be hydrogen and halogen group Z will be a chlorine atom.

A preferred vinylbenzyl chloride for incorporation into the formula-(IIc) copolymers is a material commercially available from Dow Chemical Company, Midland, Mich. Typically, the vinylbenzyl chloride will comprise a mixture of predominantly para and meta isomers, with a small content of ortho isomer. Accordingly, molecular structures illustrated herein show the essential halomethyl moiety

—$CH_2$—Z without specific assignment to one position on the phenyl ring. The copolymerizable alkenylbenzyl halide is especially useful in the production of the formula-(II) copolymers hereof, in that, the monomer exhibits good reactivity during polymerization with production of the desired copolymer. In addition, the alkenylbenzyl halides can be copolymerized with the copolymerizable azlactone monomer without undesirable interference (reaction) with the azlactone rings which are an essential part of the resulting derivatizable copolymers, i.e., the azlactone rings are not subject to ring-opening attack during the polymerization procedure.

The pendant benzyl halide moieties of the formula-(IIc) copolymers provide considerable synthetic versatility to the copolymers. Thus, the benzyl halide groups permit the copolymers to be derivatized at the halomethyl reactive sites for the purpose of introducing certain predetermined and useful activity. For example, photographically useful or therapeutically active agents can be attached to the copolymer by reaction with halomethyl groups. If desired, the halomethyl reactive sites can be reacted with agents which have the principal effect of modifying, controlling or adjusting the physical properties of the azlactone-containing copolymer. In this connection, trialkylamines can be reacted with the halomethyl reactive sites for conversion to quaternary ammonium groups which increase the hydrophilicity of the copolymer and improve wettability in aqueous systems.

The reactivity of halomethyl groups toward nucleophilic agents is well known and provides the means by which useful and active moieties can be introduced synthetically into a polymeric material. It will be appreciated that nucleophilic agents which show reactivity toward halomethyl groups, in general, will also be reactive toward azlactone rings. Such agents can be used to simultaneously derivatize the pendant halomethyl and azlactone moieties of the copolymers of the invention.

If desired, halomethyl groups of the formula-(IIc) copolymer can be reacted with an agent which shows either no reactivity or substantially no reactivity toward the pendant azlactone moieties. In this manner, predetermined functionality can be introduced at halomethyl sites while retaining the reactivity of the azlactone groups and, thus, preserving a variety of synthetic possibilities involving the azlactone groups. According to one derivatization scheme, a formula-(IIc) copolymer of the invention can be reacted with thiourea for conversion of reactive halomethyl groups to isothiouronium salt groups. Unreacted azlactone groups can then be reacted with a nucleophilic agent for incorporation, for example, of a photographically useful group, such as a diffusion control moiety of the type described in U.S. Pat. No. 4,288,523 (issued Sept. 8, 1981 to L. D. Taylor) or a diamide group of the type described in U.S. Pat. No. 3,721,565 (issued Mar. 20, 1973), useful to provide silver halide emulsion binding properties. Upon contact with aqueous alkali (e.g., during aqueous alkaline photographic processing), isothiouronium salt groups can be hydrolyzed to thiol groups to provide silver-scavenging functionality in the photographic process.

A preferred use for the formula-(IIc) copolymers of the invention involves the reaction of pendant halomethyl groups for control of the hydrophilic/hydrophobic balance of the copolymer. Inasmuch as the homopolymers of the formula-(I) 2-(4-alkenylphenyl)-5-oxazolones are water-insoluble and only poorly wetted by water, a method of preparing azlactone-containing copolymers wettable by water will be of interest. This can be accomplished by reaction of a formula-(IIc) copolymer with a tertiary amine of the formula

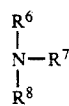

to provide a copolymer having repeating units according to the formula (IId)

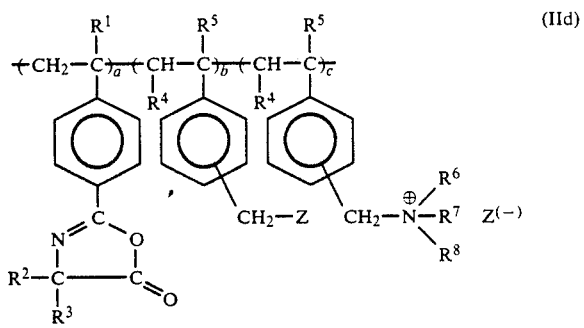

wherein each of $R^1$, $R^2$, $R^3$, $R^4$, $R^5$ and $Z$ have the meanings previously defined; each of $R^6$, $R^7$ and $R^8$ is alkyl (e.g., methyl, propyl, butyl), substituted-alkyl (e.g., hydroxyethyl, hydroxypropyl), cycloalkyl (e.g., cyclohexyl, aryl (e.g., phenyl, naphthyl), aralkyl (e.g., benzyl), alkaryl (e.g., tolyl), or at least two of $R^6$, $R^7$ and $R^8$ together with the quaternary nitrogen atom to which they are bonded complete an saturated or unsaturated, substituted or unsubstituted nitrogen-containing heterocyclic ring (e.g., morpholino, piperidino or 1-pyridyl); $Z^{(-)}$ is a counteranion (e.g., halide); and each of a, b and c represents a molar proportion of the respective repeating unit represented thereby. These copolymers have the desired functionality and versatility of the pendant azlactone groups and, as a function of control of the nature of the $R^6$, $R^7$ and $R^8$ groups, exhibit wettability by water and coatability from aqueous media.

Preferably, each of $R^6$, $R^7$ and $R^8$ will be alkyl having, for example, from 1 to 20 carbon atoms. A preferred tertiary amine for this reaction is trimethylamine and the reaction is illustrated by the following scheme (Reaction Scheme B):

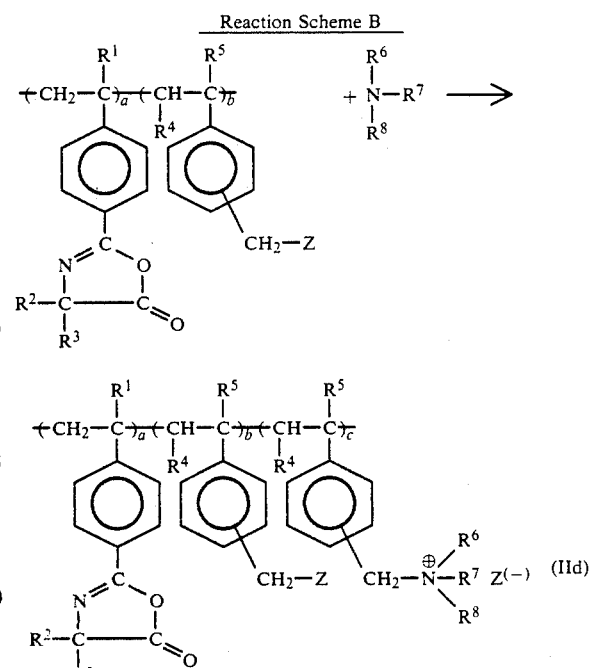

The derivatization of Reaction Scheme B can be conducted in a suitably inert organic solvent such as acetone, tetrahydrofuran, benzene, toluene, dioxane, ethyl acetate, methylethylketone, chloroform or dichloromethane. Preferably, the solvent will be anhydrous to minimize reaction with pendant azlactone groups.

It is to be noted that in the aforedescribed Reaction Scheme B, the tertiary amine reactant is non-interfering, i.e., it does not react with the pendant azlactone. As a consequence, the azlactone moieties remain intact for a subsequent and predetermined derivatization based upon the known reactivity of azlactone moieties. The tertiary amine derivatization of the formula-(IIc) copolymer converts the copolymer to one which can be wetted by water, thus, making the polymer considerably more useful for subsequent derivatization of the azlactone moieties. In addition, the tertiary amine reaction provides a polymer useful as a dye mordant for photographic systems. The formula-(IId) copolymer can be provided on a support and used as an image-receiving element in, for example, a photographic film unit of the diffusion transfer type.

The hydrophilic./hydrophobic properties observed in the formula-(IId) copolymer can be controlled in part by the amount of tertiary amine used in the reaction and by the nature of the $R^6$, $R^7$ and $R^8$ groups of the tertiary amine reactant. As can be seen from inspection of the nature of the repeating units in the formula-(IId) copolymers, unreacted (non-derivatized) vinylbenzyl halide repeating units can be present in the copolymer. The proportion of such repeating units will vary with the nature of the particular formula-(IIc) copolymer, the amount of tertiary amine used for the derivatization and the reaction conditions employed. The mole proportion of "b" repeating units can vary, for example, from zero to about 95 mole percent of the formula-(IId) copolymer. The amount of tertiary amine reactant employed can be varied to suit particular requirements and the nature of the subsequent derivatization to be performed by reaction of the azlactone moieties.

In general, it will be desired to employ an amount of tertiary amine reactant sufficient to convert most or all of the vinylbenzyl halide "b" repeating units to the corresponding ammonium-containing "c" repeating units. While tertiary amines are not, in general, reactive with azlactones per se, they do serve to catalyze nucleophilic additions to azlactones. Thus, the use of an excess of tertiary amine reactant can be employed to facilitate subsequent azlactone derivatizations without requirement of an isolation step for recovery of the formula-(IId) intermediate copolymer. Accordingly, amine derivatization of the formula-(IIc) halomethyl groups and tertiary amine-catalyzed nucleophilic additions to the formula-(IId) azlactone groups can be accomplished by one-pot methods. In some instances, it will be desirable if "b", in the formula-(IId) copolymers, is zero. Typically, however, the formula-(IId) copolymer will contain a proportion (e.g., in the range from about 0.1 mole percent to about 5 mole percent of the copolymer) of the non-derivatized vinylbenzyl halide "b" repeating units.

As indicated previously, the properties of the formula-(IId) copolymers can be controlled in part by the nature of the $R^6$, $R^7$ and $R^8$ groups of the tertiary amine used in the derivatization of reaction Scheme B. Good results can be obtained, for example, using trimethylamine or triethylamine. Hydrophobicity can be introduced using, for example, n-dodecyldimethylamine (in which case, in formula (IId), $R^6$ will be n-dodecyl and $R^7$ and $R^8$ will be methyl) or n-dodecyldiethylamine ($R^6$ is n-dodecyl and $R^7$ and $R^8$ are ethyl). Other variations in the complement of $R^6$, $R^7$ and $R^8$ can be used to control desired properties. For example, $R^6$ can be adamantyl and $R^7$ and $R^8$ can be methyl.

The properties of the formula-(IIc) and -(IId) copolymers can be substantially modified by crosslinking reactions involving pendant azlactone and/or halomethyl groups. Bifunctional crosslinking agents can be used for this purpose. For example, an aliphatic diamine can be used to effect ring opening of pendant azlactone groups and simultaneous joinder of macromolecules, as is described in the aforecited U.S. Pat. No. 3,583,950. If desired, the reaction of pendant halomethyl groups with a bifunctional crosslinking agent (such as an aliphatic diamine having $\alpha$, $\Omega$-tertiary amine groups) can be used to provide crosslinking and insolubilization. In many instances, it will be preferred to effect crosslinking by reaction of either the azlactone groups or the halomethyl groups to the exclusion of the other, so as to preserve the remaining of such reactive groups for a subsequent and predetermined derivatization. If desired, however, a bifunctional crosslinking agent which can react with both azlactone and halomethyl groups can be employed. Suitable crosslinking agents for this purpose include diamines having both primary and tertiary amine terminal groups and aromatic amines having both primary and tertiary amine substituents. Suitable crosslinking reactions (partial or complete) can be varied to suit the particular nature and properties of a copolymer material, and especially, the intended application for the resulting polymer.

As noted previously, a formula-(I) oxazolone can be homo-polymerized or copolymerized with another copolymerizable monomer and, then, derivatized by reaction, for example, with compound of the formula

or, the monomeric formula-(I) oxazolone can be first derivatized and, then, homopolymerized or copolymerized with another copolymerizable monomer. These reaction sequences can be used to provide polymers of the hereinbefore described formula (III):

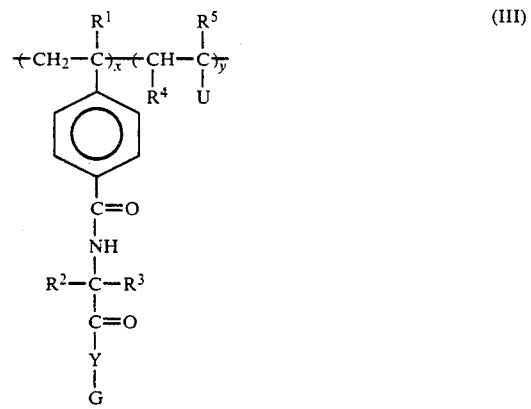

It will be appreciated that the "y" repeating units (in the case of copolymers) will be derived from an ethylenically unsaturated copolymerizable monomer which can be copolymerized with a formula-(I) monomeric oxazolone or with a derivatized monomeric oxazolone, depending upon whether the polymerization is conducted before or after azlactone-group derivatization. A variety of monomeric compounds can be used as copolymerizable monomers in the production of formula (III)

copolymers. Examples include those described hereinbefore as useful in the production of the formula-(II) polymers.

Insulation of the alkenyl polymerization functionality from the azlactone functionality is especially advantageous where a formula-(I) oxazolone is derivatized prior to polymerization, in that, Michael addition can be minimized or avoided. In general, however, it will be preferred to form a polymer (homopolymer or copolymer) having predetermined properties and to, then, react azlactone groups thereof with a suitable and predetermined derivatizating agent. Formula-(II) polymers of the invention, and particularly the copolymers, will be preferred for use according to this reaction sequence.

The formula-(II) copolymers of the invention are of particular interest for their azlactone (5-oxazolone) functionality. The reactivity of the 5-oxazolone ring with nucleophilic groups such as hydroxyl, amino and thiol groups is well known and is described, for example, in U.S. Pat. No. 3,488,327; in U.S. Pat. No. 3,583,950; in U.S. Pat. No. 4,070,348; in U.S. Pat. No. 4,288,523; in U.S. Pat. No. 4,737,560; in Great Britain Patent 1,121,418; and by Iwakura, et al., in J. Polym. Sci., A-1, 6(9), 2681 (1968). A principal and recognized advantage of azlactone compounds is that nucleophilic attack occurs without production of by-products.

Polymers of the invention can be used as intermediates for the ring-opening attachment of a variety of functional agents having an active hydrogen atom and having the formula

H—Y—G wherein Y is —O—, —NH—, —NR$^9$— or —S— (wherein R$^9$ is alkyl or aryl), and G is the residue of a nucleophilic functional agent having an active hydrogen group. The functional agent can be a dye, a photographically useful compound (e.g., a development accelerator or restrainer, or a UV stabilizer), a catalyst, or a protein (e.g., an enzyme, enzyme substrate, inhibitor, hormone, antibiotic, antibody or antigen).

The reaction of a nucleophilic substance of the aforedescribed type with a formula-(II) copolymer of the invention—to provide a functionalized polymeric material—is represented by the following scheme (Reaction Scheme C) wherein R$^1$, R$^2$, R$^3$, R$^4$, R$^5$ and T are as previously defined, and wherein the ratio of r to t is from 99:1 to 1:99 (preferably 9:1 to 1:9, especially 4:1 to 1:4).

Reaction Scheme C:

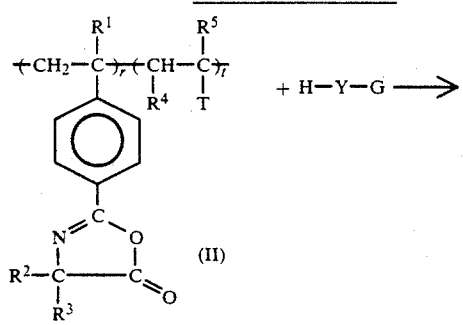

-continued
Reaction Scheme C:

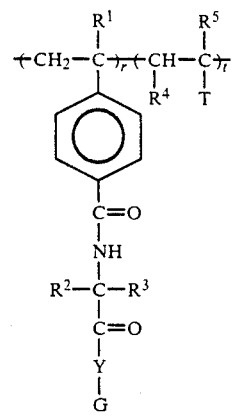

Functionalized polymeric materials of the type represented by formula (III) can be used for the useful function provided by the residue

—Y—G appended to the polymeric material. Residue —Y—G can, for example, be the residue or fragment of a dye material or other photographically useful material. Especially useful will be a photographically useful moiety that can be released in an imagewise manner from the formula-(III) polymer, such as, by a cleavage-initiating agent (e.g., silver ion, silver complex, oxidizing or reducing agent). Examples of such agents and their attachment to azlactone polymers and release therefrom are described in European Patent No. 0 073 245, published Jan. 9, 1985.

The azlactone-containing formula-(II) copolymers of the invention can be used in various biological and immunoassay methods used for the detection and measurement of proteins, metabolites, hormones, drugs, vitamins and other substances of interest (analytes) in biological and nonbiological fluids. As is disclosed, for example, in U.S. Pat. No. 4,711,840 (issued Dec. 8, 1987 to R. C. Nowinski, et al.), immunoassays generally incorporate antibodies and antigens as reactants, at least one of which is labeled with a signal-producing compound (e.g., radioisotope or fluorophore). Following mixture with the sample and incubation, specific antibody/antigen reactions occur (specific binding). The reaction mixture is subsequently interrogated to detect free and specifically bond labeled reactant, enabling a measurement of the analyte in the sample. The azlactone-containing polymers of the invention can be reacted with proteins and other agents with resulting specific binding that can be detected in accordance with the aforedescribed and generally known immunoassay methods.

The known reactivity of oxazolones with amino and hydroxyl groups affords a variety of applications for the copolymers of the present invention. The reaction of a gelatin solution and an azlactone is reported by T. Baranowski, et al., in Polonaise Des Sciences, Ch. II -Vol. XI, No. 3 (1963). Similarly, it is disclosed in U.S. Pat. No. 4,070,348 (issued Jan. 24, 1978 to D. Kraemer, et al.) that 2-isopropenyl-4,4-dimethyl-oxazolone-5 reacts with the terminal amino group of a protein. Biologically active substances, such as proteins, typically have a terminal primary amino group. These and other biologically active substances can be reacted in immunoassay and other water-based systems, using a formula-(IId) copolymer of the invention, according to the following reaction scheme (Reaction Scheme D):

Reaction Scheme D:

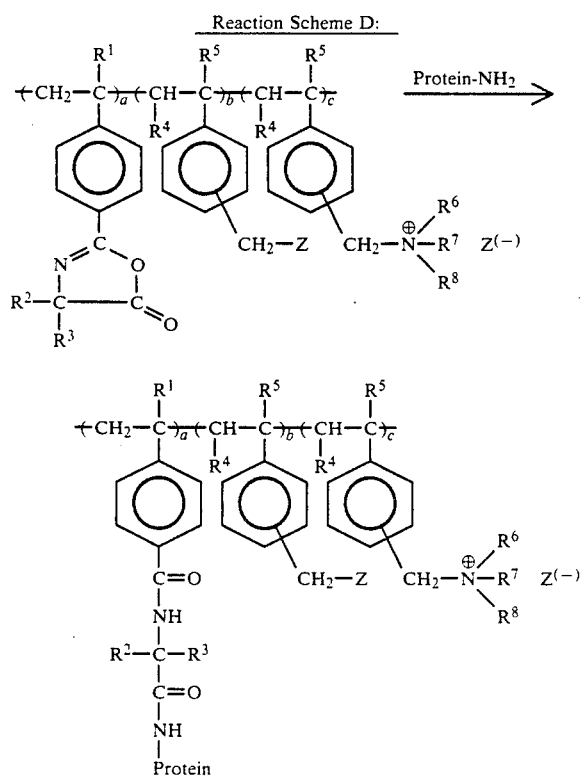

Upon reaction with enzymes, enzyme substrates, inhibitors, hormones, antibiotics, antibodies, antigens, or peptides, the azlactone groups of the formula-(IId) copolymers form covalent bonds to oxygen or nitrogen atoms, in aqueous solution at temperatures within the range of about 0° C. to 40° C. If the biologically active substances have a protein character, they have a terminal primary amino or hydroxyl group, and depending upon the particular substance, may have additional amino or hydroxyl reactive sites. The azlactone moieties are sensitive to hydroxyl reactive sites. The azlactone moieties are sensitive to hydrolysis and, if they do not react with the active substances offered, can be converted in the presence of water, into hydrophilic carboxyl or hydroxyl groups.

The following examples are illustrative of the present invention and it will be understood that the invention is not limited thereto. All parts and percentages are by weight, except as otherwise indicated. In all instances, the vinylbenzyl trialkyl ammonium chloride monomer utilized in the polymerizations was a mixture predominantly of para and meta isomers, additionally containing a small content of ortho isomer. Accordingly, the molecular structures provided in the examples to represent the vinylbenzyl trialkyl ammonium repeating units reflect the utilization of such a mixture by showing the quarternary ammonium moiety without positional specificity.

EXAMPLE 1

Part A—Preparation of p-vinylbenzoyl chloride. To an ice-cooled, dry mixture of 4-vinylbenzoic acid (40.5 g; 0.274 mole) and 50 mg of 4-t-butylpyrocatechol, 90 mls of thionyl chloride were added slowly, within a 20-second period, while stirring. The resulting suspension was allowed to rise gradually over a 15-minute period to room temperature, the evolution of hydrogen chloride gas being controlled, and was then heated for 3.5 hours at 40° to 50° C. The resulting clear solution was distilled at 90° C. (1 mm Hg) to remove excess thionyl chloride and provide the final and desired colorless product. The yield of product was 39.53 g (86.6%).

Part B—Preparation of N-(4-vinylbenzoyl)-2-methylalanine. A 250-ml, three-neck flask, equipped with a mechanical stirrer, was charged with 2-methylalanine (24.44 g; 0.237 mole); 2,6-ditertiarybutyl-p-cresol (50 mg); and 50 mls distilled water. While stirring the resulting suspension at room temperature, p-vinylbenzoyl chloride (39.5 g; 0.237 mole) and an equal volume of aqueous sodium hydroxide (18.96 g; 0.474 mole) were delivered intermittently via addition funnels, in typical Schotten-Baumann fashion, until the quantity of each was exhausted. The slightly cloudy solution was stirred for three hours and then quenched with 25 mls trifluoroacetic acid, to form a white precipitate. The isolated precipitate was washed two times (100 mls each time) with distilled water, dried under high vacuum, washed three times (400 mls each time) with boiling carbon tetrachloride, and again dried, to yield 48.5 g (82%) of a white solid at 97% purity. The product, having a melting point of about 175° C. was a compound having the following structure, confirmed by thin layer chromatographic (TLC) and nuclear magnetic resonance (NMR) analytical techniques:

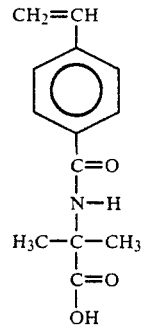

Part C—Preparation of 2-(4-vinylphenyl)-4, 4-dimethyl-5-oxazolone. A dry, one-liter, three-neck flask, equipped with a mechanical stirrer and nitrogen inlet, was charged with 40.81 g (0.175 mole) of N-(4-vinylbenzoyl)-2-methylalanine, prepared as described in Part B, and 300 mls of dry acetonitrile. Ethyl chloroformate (18.99 g; 0.175 mole) was added to the resulting suspension at room temperature and stirred for 30 minutes. The temperature was reduced to approximately 10° C. and triethylamine (35.42 g; 0.350 mole) was added dropwise over a 15-minute period. The reaction was then allowed to proceed for two hours at room temperature, followed by one hour at 40° C. Triethylamine hydrochloride was removed by filtration and the reaction supernatant was reduced under rotary evaporation to a lightly colored oil. The product was extracted from the crude product using two portions (300 mls each) of pentane. Removal of the pentane provided a white crystalline solid of greater than 97% purity, as determined by thin layer chromatography-silica gel, developed with dichloromethane. Yield was 23.5 g (63%). Analytically pure material, obtained by recrystallization from cold pentane, showed a melting point at 42°-43° C. Infrared analysis showed the characteristic azlactone carbonyl at 1820 cm⁻¹. Elemental analysis for $C_{13}H_{13}NO_2$ provided the following results.

|  | % C | % H | % N |
|---|---|---|---|
| Calculated: | 72.54 | 6.09 | 6.51 |
| Found: | 72.54 | 6.09% | 6.41 |

Nuclear magnetic resonance analysis confirmed the following structure:

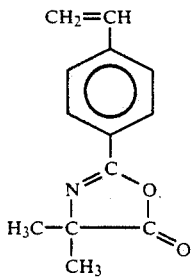

EXAMPLE 2

This example illustrates the homopolymerization of a 2-(4-alkenylphenyl)-5-oxazolone of the invention.

Into a dry, 15-ml reaction vessel, 1.0 g of 2-(4-vinylphenyl)-5-oxazolone, prepared in the manner described in Example 1, and 6.0 mls of hexane were added, followed by 10 mgs of 2,2'-azo-bis-isobutyronitrile (AIBN). The resulting reaction mixture was purged for five minutes with argon and was flame sealed and heated at 65° C. for 12 hours. The reaction vessel was cracked open to provide a white cake of material which was dissolved in 20 mls of dry acetone. The resulting solution was added slowly to 125 mls of dry hexane for precipitation of the desired polymer. Vacuum filtration yielded, on drying, a white solid in an amount of 0.94 g. The absence of vinyl protons was confirmed by proton NMR. Presence of the azlactone carbonyl at 1820 cm⁻¹ was confirmed by IR analysis.

EXAMPLE 3

This example illustrates the production of a copolymer of a 2-(4-alkenylphenyl)-5-oxazolone and an ethylenically unsatur-ated copolymerizable monomer.

Into a dry, 15-ml reaction vessel, were combined: 0.608 g (0.004 mole) of vinylbenzyl chloride; 0.431 g (0.002 mole) of 2-(4-vinylphenyl)-5-oxazolone, prepared in the manner described in Example 2; 10 mgs of AIBN; and 5 mls of dry toluene. The resulting solution was purged with argon and was flame sealed and heated at 65° C. for 20 hours. The reaction vessel was then cracked open and the contents were poured slowly into 75 mls of rapidly stirred hexanes. A white solid precipitate formed and was isolated by vacuum filtration. The product was washed with hexane and dried to yield 930 mgs of copolymer. IR analysis showed the characteristic azlactone carbonyl. Proton NMR analysis confirmed the presence of the two different aromatic repeating units of the following copolymer structure, in approximately the desired 2:1 ratio:

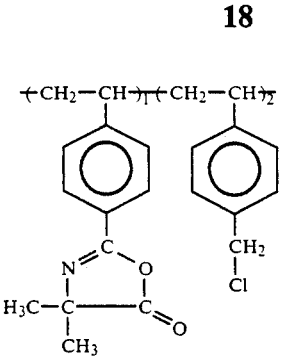

EXAMPLE 4

This example illustrates the preparation of poly(vinyl-benzyltrimethylammonium chloride-co-2-(4-vinylphenyl)-4,4-di-methyl-5-oxazolone), (2:1).

Into a dry flask equipped with a magnetic stir bar, 0.5 g of copolymer, prepared as described in Example 3 was added to 10 mls of dry acetone, under nitrogen. The temperature of the contents of the flask was reduced to −78° C. and 4.0 mls of cold trimethylamine were added immediately. The reaction vessel was tightly capped with a rubber septum while the temperature was allowed to rise slowly to 20° C. After two hours, excess trimethylamine and solvent were removed under rotary evaporation, leaving a tacky product, which on drying for 24 hours at room temperature and under high vacuum, became a clear solid. Structure was confirmed by IR analysis (KBr pellet) and the presence of the 1820 cm⁻¹ azlactone carbonyl band. Hydrolysis of the oxazolone ring to the carboxylic acid results in a shift of the carbonyl stretch to 1725 cm⁻¹. The following structure was confirmed:

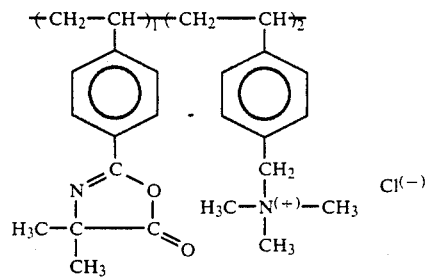

EXAMPLE 5

This example illustrates the nucleophilic ring-opening addition of a primary amine to the azlactone functionality of the monomer, 2-(4-vinylphenyl)-4,4-dimethyl-5-oxazolone.

Dimethylaminopropylamine (0.516 g; 0.00505 mole) was added to a dry solution of 2-(4-vinylphenyl)-4,4-dimethyl-5-oxazolone (1.076 g; 0.005 mole) and ten mls of hexanes, under nitrogen and at room temperature. Within seconds, product began to deposit from solution as a white precipitate. The reaction mixture was stirred for one hour. The product was isolated and characterized. Analytically pure yield was 1.4 g (88%). The product showed a melting point of 118° C. The following structure was confirmed by NMR analysis.

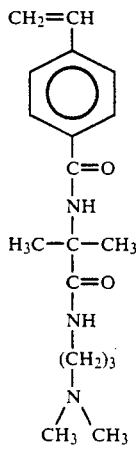

EXAMPLE 6

This example illustrates the nucleophilic ring-opening addition of histamine to the azlactone functionality of the monomer, 2-(4-vinylphenyl)-4,4-dimethyl-5-oxazolone.

Into a dry 50-ml flask, fitted with a reflux condenser, were added, under nitrogen, 2-(4-vinyl-phenyl)-4,4-dimethyl-5-oxazolone (2.16 g; 0.0105 mole), histamine (1.11 g; 0.0100 mole), and seven mls of dry chloroform. The reaction mixture was heated at 40° C. for one hour. Solvent was removed under reduced pressure, leaving a yellowish solid. After trituration with pentane and ether, the product was isolated. Purity (about 97%) was determined by thin layer chromatography, silica eluted with methylene chloride/methanol (20:5). Yield was 2.6 g (80%). The product showed the onset of melting at 46° C. accompanied by polymerization. The following structure was confirmed by NMR analysis.

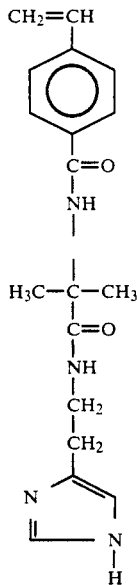

EXAMPLE 7

This example illustrates the nucleophilic ring-opening addition of diethylamine to the azlactone functionality of the monomer, 2-(4-vinylphenyl)-4,4-dimethyl-5-oxalone.

A dry 25-ml flask was charged with 2-(4-vinylphenyl)-4,4-dimethyl-5-oxazolone (0.538 g; 0.00250 mole), six mls of dry hexanes, and 0.264 ml of diethylamine (0.1865 g; 0.00255 mole). The reaction vessel was capped and stirred under nitrogen for four hours at room temperature, followed by 20 hours at 40° C. A white precipitate (100 mgs) was isolated from the reaction and was washed with hexane. The structure of the desired product was confirmed by NMR analysis. The resulting low yield prompted the addition of one equivalent of diethylamine to the reaction supernatant and reaction for 20 hours at 40° C., to yield an additional 110 mgs of the desired product (yield 20%). Purity was established (at about 90%) by thin layer chromatography (TLC). IR and NMR analysis confirmed the following structure:

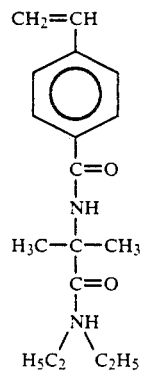

EXAMPLE 8

This example illustrates the copolymerization of styrene and the derivatized monomer prepared in Example 6.

Into a 20-ml sealable reaction vessel were added, five mls of dry dimethylformamide and 1.63 g (0.005 mole) of the monomer prepared as described in Example 6. Styrene (1.04 g; 0.001 mole) and 21 mgs of AIBN were added and the reaction mixture was purged for 15 minutes with argon. The vessel was flame sealed and heated at 60° C. for 20 hours. The vessel was then cracked open, whereupon, the contents were added slowly to 150 mls of rapidly stirred ethylacetate. A light-yellow precipitate formed and was isolated by vacuum filtration. The product was dried under high vacuum to yield 1.62 g of polymer (60% of the expected total mass yield). The absence of vinylic protons and the following structure were confirmed by NMR analysis:

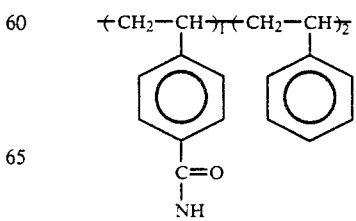

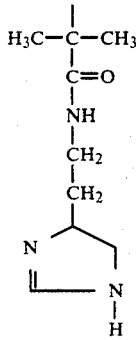

EXAMPLE 9

This example illustrates the nucleophilic ring-opening addition of an anthraquinone magenta dye to the monomer, 2-(4-vinylphenyl)-4,4-dimethyl-5-oxazolone.

A dry, 50-ml, round-bottom flask was charged with eight mls of dry dimethylsulfoxide; 1,4-diaminoanthraquinone-2-[5-amino-pentyloxy](0.3394 g; 0.0010 mole); and 2-(4-vinylphenyl)-4,4-dimethyl-5-oxazolone (0.2368 g; 0.0011 mole). The reaction mixture was stirred at room temperature under nitrogen for 2.5 hours. Reaction progression was monitored by TLC: silica gel, eluted with methylene chloride/methanol (20:2). Product $R_f$ was about 0.8. The mixture was added slowly to 150 mls of rapidly stirring water. The desired product precipitated and was isolated by vacuum filtration. Following a water wash, the highly colored (magenta) solid was dried under high vacuum, to yield 527 mgs (0.0095 mole) of product at about 95% yield. Approximately 8% contamination from excess 2-(4-vinylphenyl)-4,4-dimethyl-5-oxazolone monomer was present, as determined by proton NMR. Removal of the monomer can be accomplished by extending the hydrolysis time during isolation of the product. The expected 5-amino-acylated product, of the following structure, was confirmed by proton NMR, UV and IR:

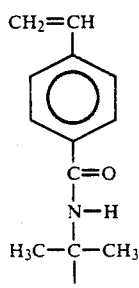

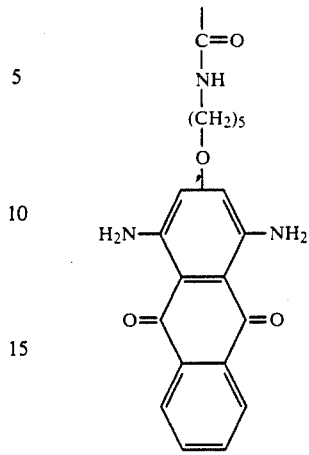

EXAMPLE 10

This example illustrates an alternative method of preparing the product of Example 7.

A dry, 25-ml flask was charged with VPDMO (1.2 g; 0.00557 mole) and five mls of diethylamine. The reaction was capped under argon and heated for 20 hours at 40° C. Excess diethylamine was removed under reduced pressure leaving a lightly colored oil. The crude oil was taken up in 60 mls of methylene chloride, was extracted with 50 mls of 2.0 Normal sodium hydroxide, followed by 50 mls of saturated brine and was dried over sodium sulfate. An additional 50 mls of methylene chloride were added to the organic layer and the resulting solution was mixed thoroughly with a 100-ml volume of silica gel (32-63 micron). The silica gel was washed twice with methylene chloride (100 mls each) and the product was eluted from the gel with methylene chloride/methanol (3/2). Solvent was removed under reduced pressure, to provide a tacky orange solid. After drying under reduced pressure, 1.10 g of product (68% yield) was obtained at a purity of about 97%. Structure was confirmed by proton NMR.

COMPARATIVE EXAMPLE

For purposes of comparison with the diethylamine-derivatization of 2-(4-vinylphenyl),4,4-dimethyl-5-oxazolone (VPDMO), as described in Example 10, a diethylamine-derivatization of 2-vinyl-4,4-dimethyl-5-oxazolone (VDMO) was attempted in the following manner. Reaction conditions were identical to those described in Example 10, except that, one gram of VDMO was used in place of VPDMO. The silica treatment was not applied since chromatographic analysis of the crude product was not as easily interpreted, due to lack of UV absorption. The absence of vinyl protons between 5-7 ppm was confirmed by proton-NMR analysis of the crude product—leading to the conclusion that diethylamine added to the vinyl group of VDMO by Michael addition.

What is claimed is:

1. A 2-(4-alkenylphenyl)-5-oxazolone compound having the formula (I)

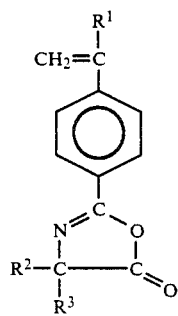

(I)

wherein $R^1$ is hydrogen or alkyl; each of $R^2$ and $R^3$ is hydrogen, alkyl, aryl, alkaryl, aralkyl, cycloalkyl, or $R^2$ and $R^3$ together with the carbon atom to which they are bonded constitute a ring.

2. The compound of claim 1 wherein $R^1$ is hydrogen.

3. The compound of claim 1 wherein each of $R^2$ and $R^3$ is alkyl.

4. The compound of claim 3 wherein each of $R^2$ and $R^3$ is methyl.

5. The compound of claim 1 wherein $R^1$ is hydrogen and each of $R^2$ and $R^3$ is methyl.

* * * * *